(12) United States Patent
Pettit et al.

(10) Patent No.: US 10,729,385 B2
(45) Date of Patent: Aug. 4, 2020

(54) ORTHOTIC DEVICES FOR MONITORING POSTURAL INFORMATION ASSOCIATED WITH A HUMAN BODY

(71) Applicants: Andrew Timothy Pettit, Santa Clara, CA (US); Jason Joseph Wong, Naples, FL (US)

(72) Inventors: Andrew Timothy Pettit, Santa Clara, CA (US); Jason Joseph Wong, Naples, FL (US)

(73) Assignees: Andrew T. Pettit, Austin, TX (US); Jason Joseph Wong, Naples, FL (US)

( * ) Notice: Subject to any disclaimer, the term of this patent is extended or adjusted under 35 U.S.C. 154(b) by 296 days.

(21) Appl. No.: 15/948,856

(22) Filed: Apr. 9, 2018

(65) Prior Publication Data
US 2018/0228446 A1    Aug. 16, 2018

Related U.S. Application Data

(63) Continuation of application No. 13/936,109, filed on Jul. 5, 2013, now Pat. No. 9,936,921.

(60) Provisional application No. 61/668,125, filed on Jul. 5, 2012.

(51) Int. Cl.
| | | |
|---|---|---|
| A61B 5/00 | (2006.01) | |
| A61F 5/02 | (2006.01) | |
| A61B 5/11 | (2006.01) | |

(52) U.S. Cl.
CPC .......... *A61B 5/7275* (2013.01); *A61B 5/0002* (2013.01); *A61B 5/0004* (2013.01); *A61B 5/1112* (2013.01); *A61B 5/1116* (2013.01); *A61B 5/4836* (2013.01); *A61B 5/6823* (2013.01); *A61F 5/026* (2013.01); *A61F 5/028* (2013.01); *A61B 5/746* (2013.01)

(58) Field of Classification Search
CPC ......... A61F 5/028; A61F 5/026; A61B 5/6823
See application file for complete search history.

(56) References Cited

U.S. PATENT DOCUMENTS

| | | | | |
|---|---|---|---|---|
| 5,346,461 | A | * 9/1994 | Heinz ..................... | A61F 5/028 128/121.1 |
| 6,137,675 | A | * 10/2000 | Perkins .................. | G06F 1/163 128/876 |
| 6,827,694 | B2 | 12/2004 | Gladoun | |
| 7,431,703 | B2 | 10/2008 | Salvi et al. | |
| 8,018,346 | B2 | * 9/2011 | Gottlieb ............. | G08B 21/0446 340/573.7 |

(Continued)

*Primary Examiner* — Matthew F Desanto
(74) *Attorney, Agent, or Firm* — Perkins Coie LLP

(57) ABSTRACT

Apparatuses and methods for the prevention of bodily injuries through active monitoring of bodily postures, supporting a body while in or restricting a body from entering predetermined postures which heighten the body's susceptibility to injury, and alerting one or more entities (e.g., an apparatus user) of a body's susceptibility to injury is disclosed herein. In one embodiment, the method may include one or more operations including monitoring one or more bodily postures and/or bodily movements, storing data associated with bodily postures and/or bodily movements, determining a risk of injury associated with bodily postures and/or bodily movements, and alerting one or more entities when a risk of injury associated with bodily postures and/or bodily movements reaches a predetermined level.

18 Claims, 8 Drawing Sheets

(56) References Cited

U.S. PATENT DOCUMENTS

| | | | |
|---|---|---|---|
| 2005/0043660 A1* | 2/2005 | Stark | A61F 5/0106 |
| | | | 602/19 |
| 2006/0282021 A1 | 12/2006 | DeVaul et al. | |
| 2009/0254003 A1* | 10/2009 | Buckman | A61B 5/1117 |
| | | | 600/595 |
| 2010/0268140 A1 | 10/2010 | Berlese | |
| 2010/0313329 A1* | 12/2010 | Haynes | A41D 13/0012 |
| | | | 2/102 |
| 2011/0063114 A1* | 3/2011 | Ikoyan | A63B 21/4007 |
| | | | 340/573.7 |
| 2011/0082393 A1* | 4/2011 | Bort | A61F 5/026 |
| | | | 600/594 |
| 2011/0230806 A1* | 9/2011 | Lou | A61F 5/012 |
| | | | 602/13 |
| 2011/0295159 A1 | 12/2011 | Shachar et al. | |
| 2012/0112923 A1* | 5/2012 | Chupa | G08B 13/1672 |
| | | | 340/686.1 |
| 2012/0174302 A1 | 7/2012 | Jenkins, III | |
| 2012/0246795 A1* | 10/2012 | Scheffler | A41D 13/1281 |
| | | | 2/69 |
| 2012/0292363 A1* | 11/2012 | Crawford | A45F 5/02 |
| | | | 224/655 |
| 2013/0201021 A1 | 8/2013 | Limonadi et al. | |
| 2013/0312150 A1* | 11/2013 | Klein | A45F 3/06 |
| | | | 2/2.5 |
| 2013/0331755 A1* | 12/2013 | Rotblatt | A61F 5/028 |
| | | | 602/19 |
| 2013/0345612 A1* | 12/2013 | Bannister | A61B 5/1116 |
| | | | 602/19 |
| 2014/0099615 A1* | 4/2014 | Sweeney | A61B 5/7405 |
| | | | 434/254 |

* cited by examiner

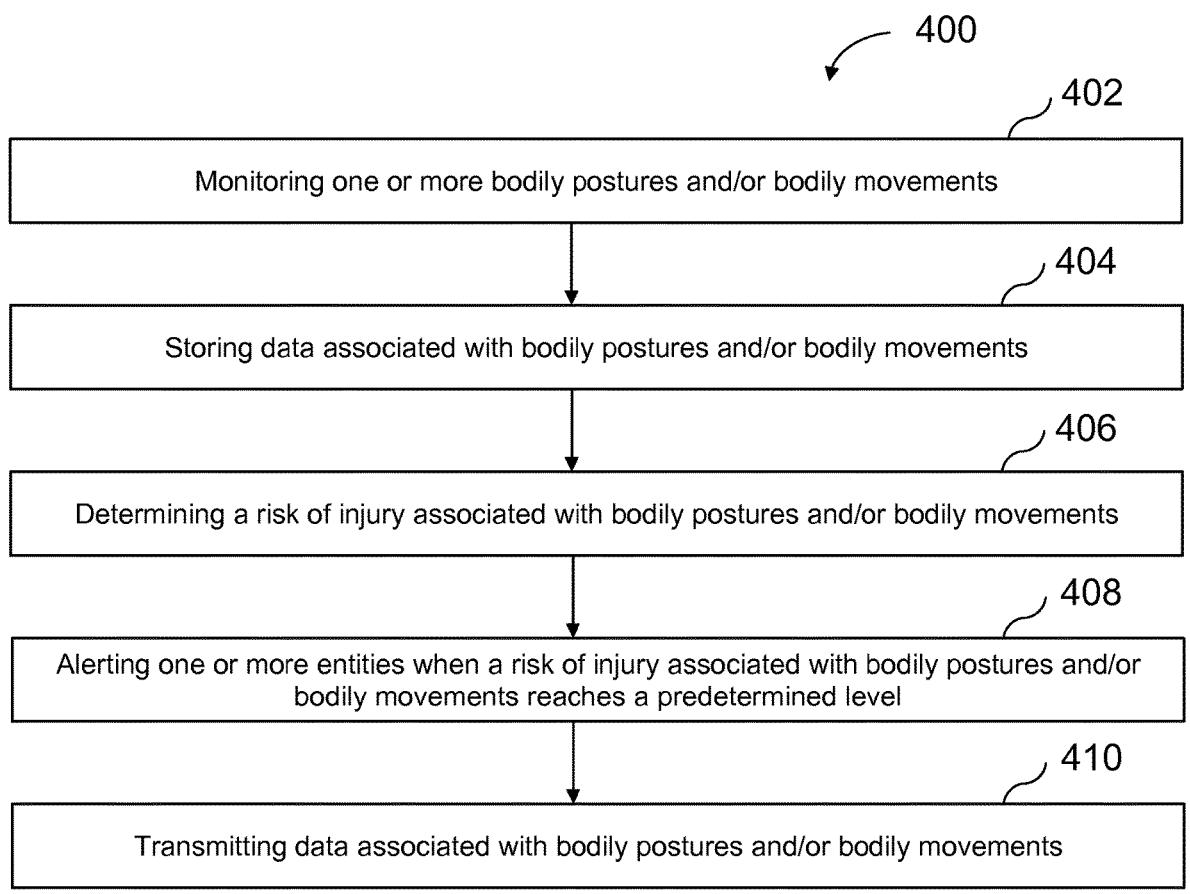

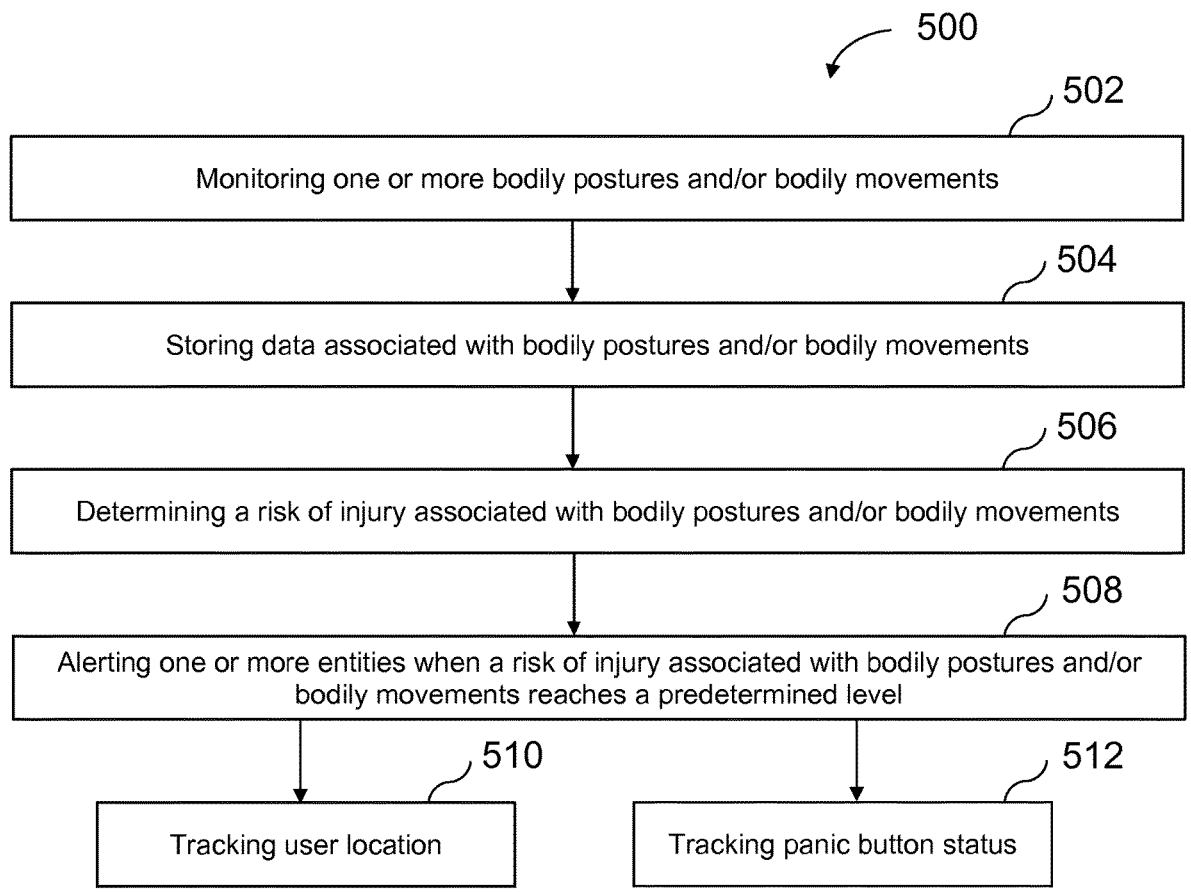

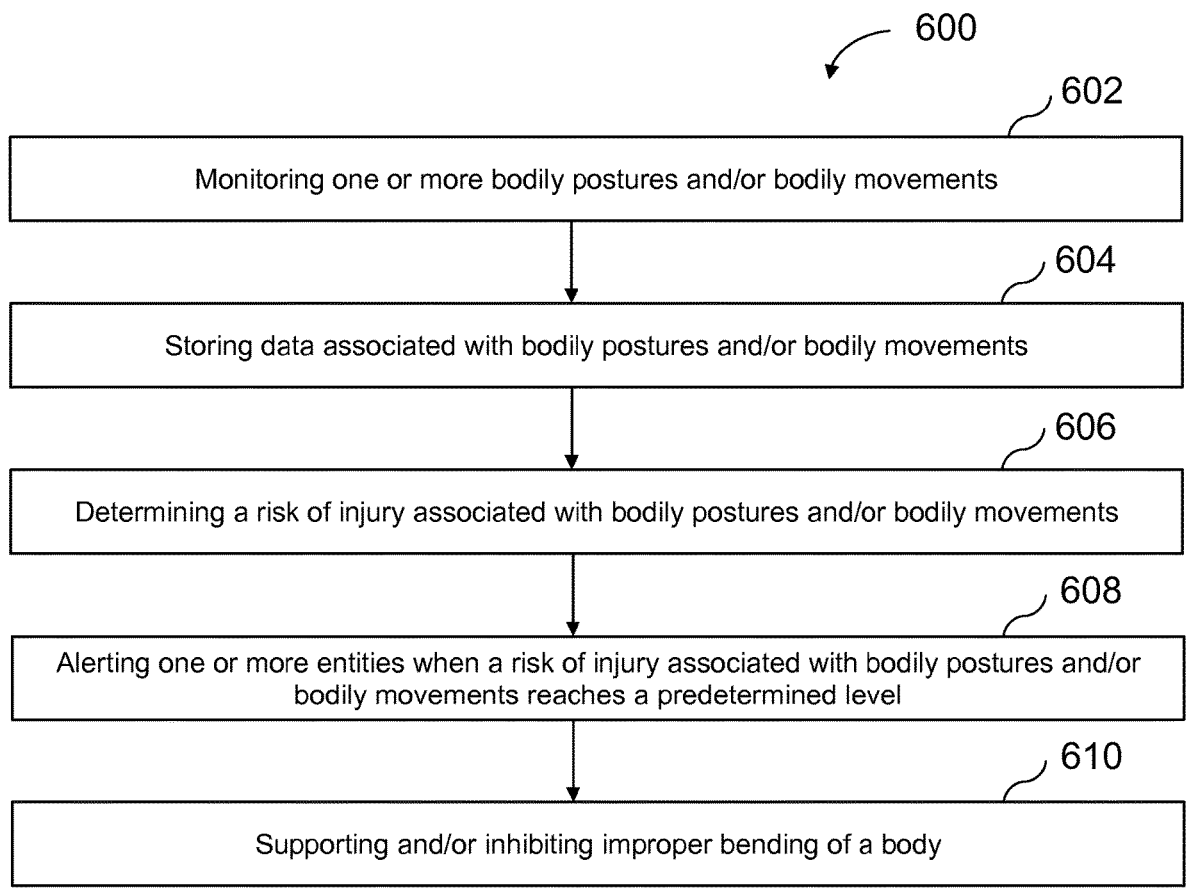

702 computer readable media 704 one or more software applications 706 operations of
monitoring one or more bodily postures and/or bodily movements;
storing data associated with bodily postures and/or bodily movements;
determining a risk of injury associated with bodily postures and/or bodily movements;
and
alerting one or more entities when a risk of injury associated with bodily postures and/or bodily movements reaches a predetermined level

ORTHOTIC DEVICES FOR MONITORING POSTURAL INFORMATION ASSOCIATED WITH A HUMAN BODY

CROSS-REFERENCE TO RELATED APPLICATIONS

This application is a continuation of U.S. patent application Ser. No. 13/936,109, filed on Jul. 5, 2013, which claims the priority of U.S. Provisional Application No. 61/668,125, filed on Jul. 5, 2012, each of which is incorporated herein in its entirety by reference thereto.

FIELD OF THE DISCLOSURE

This disclosure relates to the field of injury prevention, and more specifically, to apparatuses and methods for the prevention of bodily injuries through the use of medical electronics.

INTRODUCTION

A market currently exists for apparatuses related to the prevention of injuries, especially injuries resulting from certain forms of physical labor. Employers actively seek out solutions to reduce costs associated with workplace injuries (e.g., over one hundred million dollars is spent annually on preventive back braces). Generally, the market is comprised of a multitude of normal restrictive-type back braces, most of which can be classified as one of either an industrial back support or a medical back brace. Industrial back supports, which are made of soft and relatively flexible material, are commonly worn by laborers whose occupation increases their susceptibility to back injuries (e.g., a high percentage of nursing aides and truck drivers suffer from back injuries and, therefore, many in these industries choose to wear industrial back supports for injury prevention). Medical back braces, which may be either soft or rigid through the inclusion of inflexible members, are commonly prescribed by medical professionals to patients post-injury or post-surgery. Neither industrial back supports nor medical back braces are effective in actual injury prevention.

There are a variety of support structures that disclose a lumbar back brace support member for a back brace support belt (e.g., a rigid support providing additional axial support to the lumbar region). However, due to the nature of the internal bodily stresses associated with the certain forms of physical labor (e.g., stress on the lower back from repeatedly leaning forward and lifting), the addition of a rigid member to a traditional back brace is ill suited to prevent physical labor injuries. During a two year study reported in December 2000 by the National Institute for Occupational Safety and Health (NIOSH), NIOSH found no statistically significant difference in either the incidence of workers compensation claims or self-reported pain between workers who wore back support belts daily and those who rarely or never wore back support belts. The study also found that, although back support belts restrict certain movements, they do not have that effect when the worker bends forward as in many industrial lifting situations. Back support belts, even those including rigid support members, do nothing to prevent a physical laborer from entering certain postures known to be contributing factors to bodily injury. Even if such demobilization were incorporated into a back support belt the apparatus would be highly uncomfortable.

Another conventional approach to preventing back injuries provides a back bend monitoring system designed to actively monitor and sense vertebral movement (e.g., the changing of the shape of the L1-L5 vertebrae, lumbar vertebrae, area from concave to either a straight or a convex shape). In such an approach, the system is deployed on or adjacent to a portion of a person's lower back, and can use electronic sensors to monitor the amount of bending of the lower back. While these systems are capable of monitoring and sensing certain bending in the lumbar vertebrae, such bending comprises but one of many factors known to contribute to bodily injury. Thus, in a typical back bend monitoring system that utilizes this approach, the system fails to account for any additional factors that may contribute to the user's susceptibility to injury.

SUMMARY

The present preferred embodiments are apparatuses and methods for the prevention of bodily injuries through active monitoring of bodily postures, supporting a body while in and/or restricting a body from entering predetermined postures which heighten the body's susceptibility to injury, and alerting one or more entities (e.g., an apparatus user) of a body's past, current, or expected future susceptibility to injury is disclosed herein. Examples of data that may be monitored include, but are not limited to, tilt, torsion, and rotation of the user's lumbar region. The apparatuses and methods for the prevention of bodily injuries can be used to alert the apparatus user or others that certain postures (e.g., a posture the apparatus user is currently in) have heightened the user's susceptibility to injury thus giving the user the opportunity to refrain from lifting from that posture. The apparatuses and methods for the prevention of bodily injuries can also be used to provide information to one or more entities other than the apparatus user (e.g., a delivery company that employs the apparatus user to load delivery vehicles) of certain jobs and/or employees in which the risk of injury is heightened.

In one embodiment, the method may include one or more operations including monitoring one or more bodily postures and/or bodily movements, storing data associated with bodily postures and/or bodily movements, determining a risk of injury associated with bodily postures and/or bodily movements, and alerting one or more entities when a risk of injury associated with bodily postures and/or bodily movements reaches a predetermined level. Therefore, the apparatus and methods for the prevention of bodily injuries solves the long-felt need of providing information associated with bodily stresses prior to the onset of injury; this information enables preventive measures rather than reactive measures to be taken with regard to injuries caused by physical labor.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 4 depicts a block diagram of a method for the prevention of bodily injuries according to an embodiment of the invention.

FIG. 5 depicts a block diagram of a method for the prevention of bodily injuries according to an embodiment of the invention.

FIG. 6 depicts a block diagram of a method for the prevention of bodily injuries according to an embodiment of the invention.

FIG. 7 is a system diagram of one or more software applications embodied in computer readable media for preventing bodily injuries.

DETAILED DESCRIPTION

Figure 1:
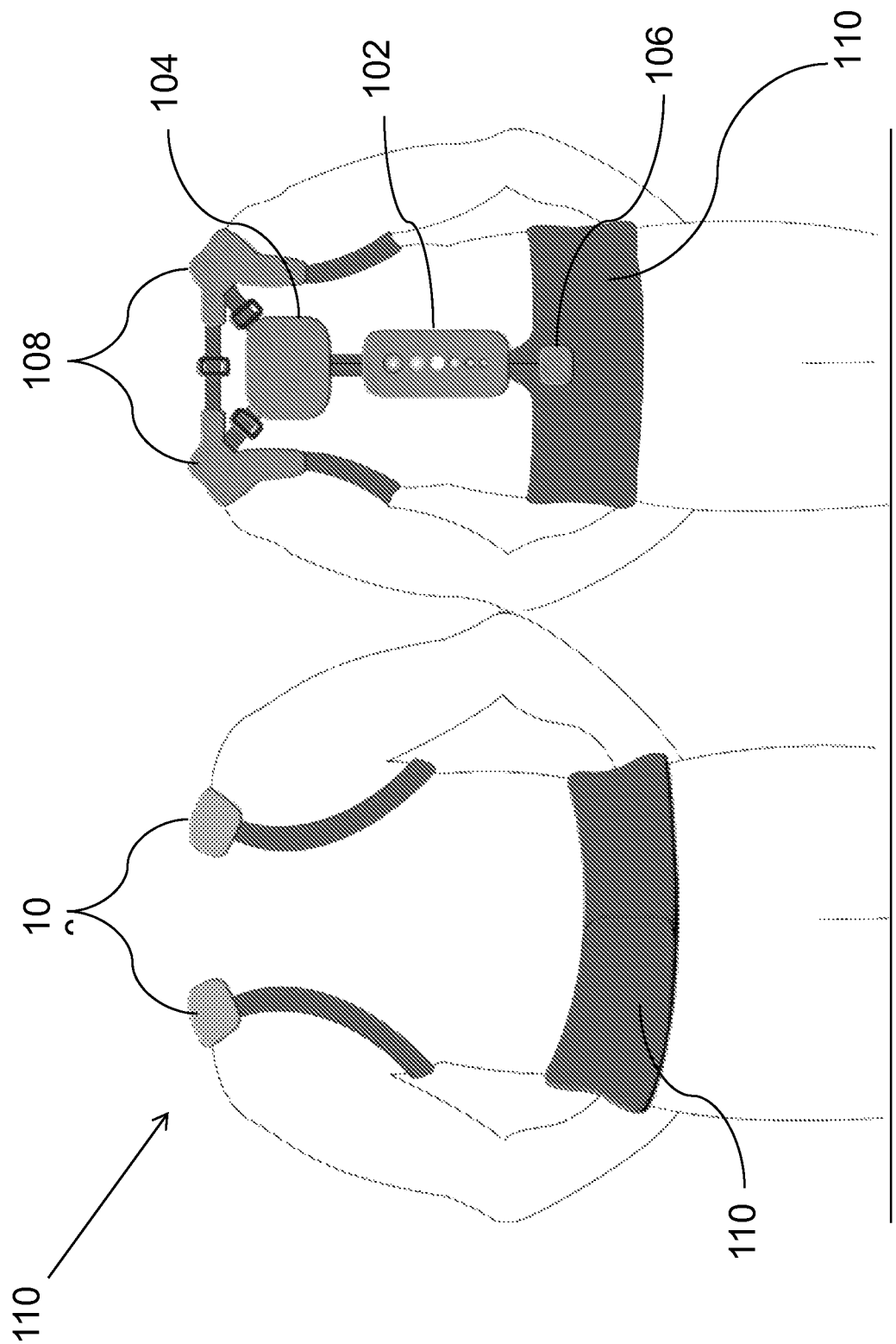
FIG. 1a depicts a front view of an apparatus for the prevention of bodily injuries according to an embodiment of the invention.
FIG. 1b depicts a back view of an apparatus for the prevention of bodily injuries according to an embodiment of the invention.

Apparatuses and methods for the prevention of bodily injuries through active monitoring of bodily postures, supporting a body while in and/or restricting a body from entering predetermined postures which heighten the body's susceptibility to injury, and alerting one or more entities (e.g., an apparatus user) of a body's past, current, or expected future susceptibility to injury are described within the Detailed Description below.

Various aspects of the invention will now be described. The following description provides specific details for a thorough understanding and enabling description of these examples. One skilled in the art will understand, however, that the invention may be practiced without many of these details. Additionally, some well-known structures or functions may not be shown or described in detail, so as to avoid unnecessarily obscuring the relevant description. Although the diagrams depict components as functionally separate, such depiction is merely for illustrative purposes. It will be apparent to those skilled in the art that the components portrayed in these figures may be arbitrarily combined or divided into separate components.

The terminology used in the description presented below is intended to be interpreted in its broadest reasonable manner, even though it is being used in conjunction with a detailed description of certain specific examples of the invention. Certain terms may even be emphasized below; however, any terminology intended to be interpreted in any restricted manner will be overtly and specifically defined as such in this Detailed Description section.

Specific details of certain embodiments of the apparatuses and methods for the prevention of bodily injuries are set forth in the following description and in FIGS. 1-8 to provide a thorough understanding of such embodiments. The present apparatus and methods for the prevention of bodily injuries may have additional embodiments, may be practiced without one or more of the details described for any particular described embodiment, or may have any detail described for one particular embodiment practiced with any other detail described for another embodiment.

FIG. 1*a* and FIG. 1*b* depict a front view and back view, respectively, of an apparatus for the prevention of bodily injuries 100 according to an embodiment of the invention. In the example of FIG. 1*a*, apparatus 100 may include one or more elements including a main housing 102, a secondary upper housing 104, a secondary lower housing 106, a torso support module 108, and a lumbar support module 110. The following embodiments and descriptions are for illustrative purposes only and are not intended to limit the scope of the apparatuses and methods for the prevention of bodily injuries.

In one embodiment, the main housing 102, shown in FIG. 1*b*, comprises one or more sensors placed within the cavity of the housing. In an alternative embodiment the sensors may be adjacent to or coupled to the main housing 102. The sensor may be an inclinometer for measuring tilt of the back, yaw sensors for measuring torsion and rotation of the back, or an accelerometer configured to measure tilt, torsion or rotation of the back. For example, the sensors may be Level Developments LCP-45 Dual Axis Inclinometer Sensors or iMEMS®. ADXL330 3-Axis Accelerometers, data sheets of which are publically available. As used herein, tilt is defined as a sloping position or movement. Generally, tilt is measured by positioning a sensing device (e.g., an inclinometer) adjacent to a predetermined portion of a body and measuring the slope with respect to one or more of the sagittal plane, the coronal plane, the transverse plane, and/or any combination thereof. Any of the features described here may be included in either the secondary upper housing 104 and/or the secondary lower housing 106 in alternative embodiments.

In some embodiments, the main housing 102 comprises a power source (e.g., a rechargeable and/or removable battery). Preferably, the power source is both rechargeable and a standard battery size such that replacing batteries is not typically necessary yet the apparatus can still be utilized if charging is not an option by using standard batteries. In another embodiment, the main housing 102 may have an interface capable of connecting to a voltage supply. For example, the main housing 102 may comprise an female power connector that is capable of connecting to a Universal Serial Bus (USB) cable or male power connector cable. Any of the features described here may be included in either the secondary upper housing 104 and/or the secondary lower housing 106 in alternative embodiments.

One embodiment of the apparatus 100 requires a memory storage device be placed within the cavity of either the main housing 102, the secondary upper housing 104, and/or the secondary lower housing 106. Additionally, all data registered by the at least one sensor described above may be preserved for a specific timeframe. As discussed above, one skilled in the art would appreciate the various manners in which the apparatus 100 could record and transmit data. One alternative embodiment may include a removable memory storage device (e.g., USB drive, Secure Digital (SD) non-volatile memory card) that can be used to upload all recorded sensor data to the user's personal computer. Another alternative embodiment may include wireless local area network (WLAN) or Bluetooth®. transmitter circuits that enable transmission of WLAN/Bluetooth® signals from the apparatus 100 to the user's personal computer or a data server.

In one preferred embodiment, the torso support module 108 is arranged to enclose, at least partly, the user's upper back and chest. For example, the torso support module 108 may be shoulder straps designed to allow the secondary upper housing 104 to rest comfortably adjacent to the upper back of the user. One or more sensors designed to monitor movement of the upper back may be coupled to the torso support module 108. In one embodiment, at least one strain gauge for measuring flexion and/or extension of the spine and/or upper extremities may be used. For example, at least one strain gauge may be placed adjacent to the torso support module 108 such that when a user leans forward the strain gauge material is lengthened, thereby increasing the resistance reading across said strain gauge material; this allows a central processing unit to determine the posture and/or bodily movements associated with the resistance reading across the strain gauge material. In another preferred embodiment, the lumbar support module 110 is arranged to enclose the user's lumbar region and waist. For example, the lumbar support module 110 may be a semi-rigid back support designed to restrict movement of the lower back and allow the secondary lower housing 106 to rest comfortably adjacent to the lower back of the user. Conversely, the lumbar support module 110 may be a non-rigid waist belt shaped in order to better adhere the apparatus 100 to the user's lower back profile.

Figure 2:
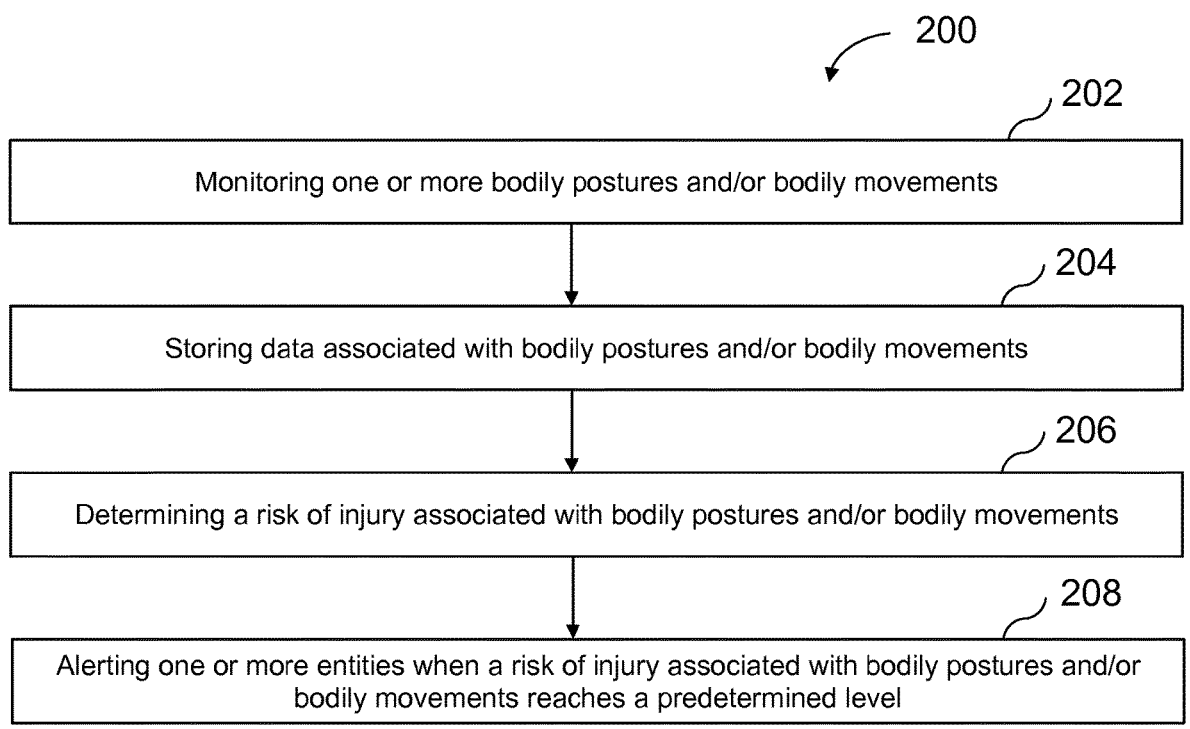
FIG. 2 depicts a block diagram of a method for the prevention of bodily injuries according to an embodiment of the invention.

FIG. 2 depicts a block diagram of a method for the prevention of bodily injuries according to an embodiment of the invention. In one embodiment, method 200 may include one or more operations including monitoring one or more bodily postures and/or bodily movements 202, storing data associated with bodily postures and/or bodily movements 204, determining a risk of injury associated with bodily postures and/or bodily movements 206, and alerting one or more entities when a risk of injury associated with bodily postures and/or bodily movements reaches a predetermined level 208. The following embodiments and descriptions are for illustrative purposes only and are not intended to limit the scope of the apparatuses and methods for the prevention of bodily injuries.

Monitoring one or more bodily postures and/or bodily movements at block 202 may be performed by one or more sensing devices such as strain gauges, inclinometers, accelerometers, gyroscopes, or yaw sensors. For example, sensing devices for monitoring one or more bodily postures and/or bodily movements may include a high elongation strain gauge for measuring flexion and/or extension of the upper back, an inclinometer for measuring tilting of the upper body, and accelerometers for measuring tilt, torsion and rotation of the lumbar area. In some embodiments, monitoring one or more bodily postures and/or bodily movements at block 202 may include monitoring for data associated with predetermined bodily postures, predetermined bodily movements, the speed and/or repetitiveness at which predetermined bodily postures are entered, the speed and/or repetitiveness at which predetermined bodily movements are executed, or any combination thereof. Other types of sensing devices known in the art may be used.

In some embodiments, storing data associated with bodily postures and/or bodily movements at block 204 may be performed by one or more data storage devices such as semiconductor memory, magnetic storage, and optical storage. For example, storage devices for storing data associated with bodily postures and/or bodily movements may include an SD non-volatile memory card. Preferably, the storage device is both of an industrial standard format, non-volatile, and also removable (e.g., an SD card, a USB flash drive) in order to ensure that the data associated with bodily postures and/or bodily movements is lasting and easily accessible. Other types of data storage devices known in the art may also be used.

In some embodiments, determining a risk of injury associated with bodily postures and/or bodily movements at block 206 may be performed by one or more central processing units (CPU), one or more human beings, or any combination thereof. For example, a CPU may calculate the risk of injury associated with bodily postures and/or bodily movements using one or more predetermined algorithms, or, alternatively, a human being might determine the risk of injury associated with bodily postures and/or bodily movements through examination of data associated with bodily postures and/or bodily movements. In some embodiments, the risk of injury will be determined to be heightened in the event that certain bodily postures and/or bodily movements sensed indicate that a user is lifting items that are heavier or larger than allowable. For example, because people tend to use heft and/or certain identifiable bodily postures and/or bodily movements to lift heavy items, the operation of determining a risk of injury associated with bodily postures and/or bodily movements at block 206 may take such data into account. In some embodiments, the risk of injury will be determined by accounting for certain bodily postures and/or bodily movements independent of other different bodily postures and/or bodily movements. For example, the risk of injury determined due to a predetermined level of strain in the lower back may remain unchanged even with the addition of a level of yaw in the lower back. In some embodiments, the risk of injury will be determined by accounting for certain bodily postures and/or bodily movements in aggregation with other different bodily postures and/or bodily movements. For example, the risk of injury determined due to a certain predetermined level of strain in the lower back may be less when that strain is the only factor contributing to the risk of injury. In such an embodiment, holding all but one of the factors contributing to the risk of injury equal while increasing/decreasing the severity of the risk contributed by that factor will increase/decrease the overall determined risk of injury. In some embodiments, the risk of injury will be determined by monitoring for certain threshold levels of risk associated with one or more bodily postures and/or bodily movements, or any combination thereof. For example, the determined risk level for a predetermined bodily posture may remain unchanged regardless of the duration of which the bodily posture is maintained. In different embodiments, the risk of injury will be determined by accounting for the potential effects of body and/or mental fatigue occurring over the course of time. For example, the determined risk of injury may increase over the course of time even when the bodily postures and/or bodily movements sensed have remained identical. Generally, embodiments which account for the potential effects of body and/or mental fatigue are preferred because many workplace injuries occur due to the repetition of certain bodily postures and/or bodily movements.

In some embodiments, alerting one or more entities when a risk of injury associated with bodily postures and/or bodily movements reaches a predetermined level at block 208 may be performed through a physical means, visual means, audible means, electronic means, or any combination thereof. For example, an alerted entity may be the user of the apparatus embodying the disclosed method and the entity may be alerted by a prerecorded voice which recites the current level of risk and recommends ceasing further physical activity. Additionally, an alerted entity may be an employer or a regulatory agency which is alerted of a level of risk of injury through the receipt of electronic data (e.g., receiving an email notification). Generally, embodiments which alert both the user of the apparatus embodying the disclosed method as well as an employer are preferable because such embodiments may facilitate the elimination of the need for or the occurrence of certain bodily postures and/or bodily movements.

Figure 3:
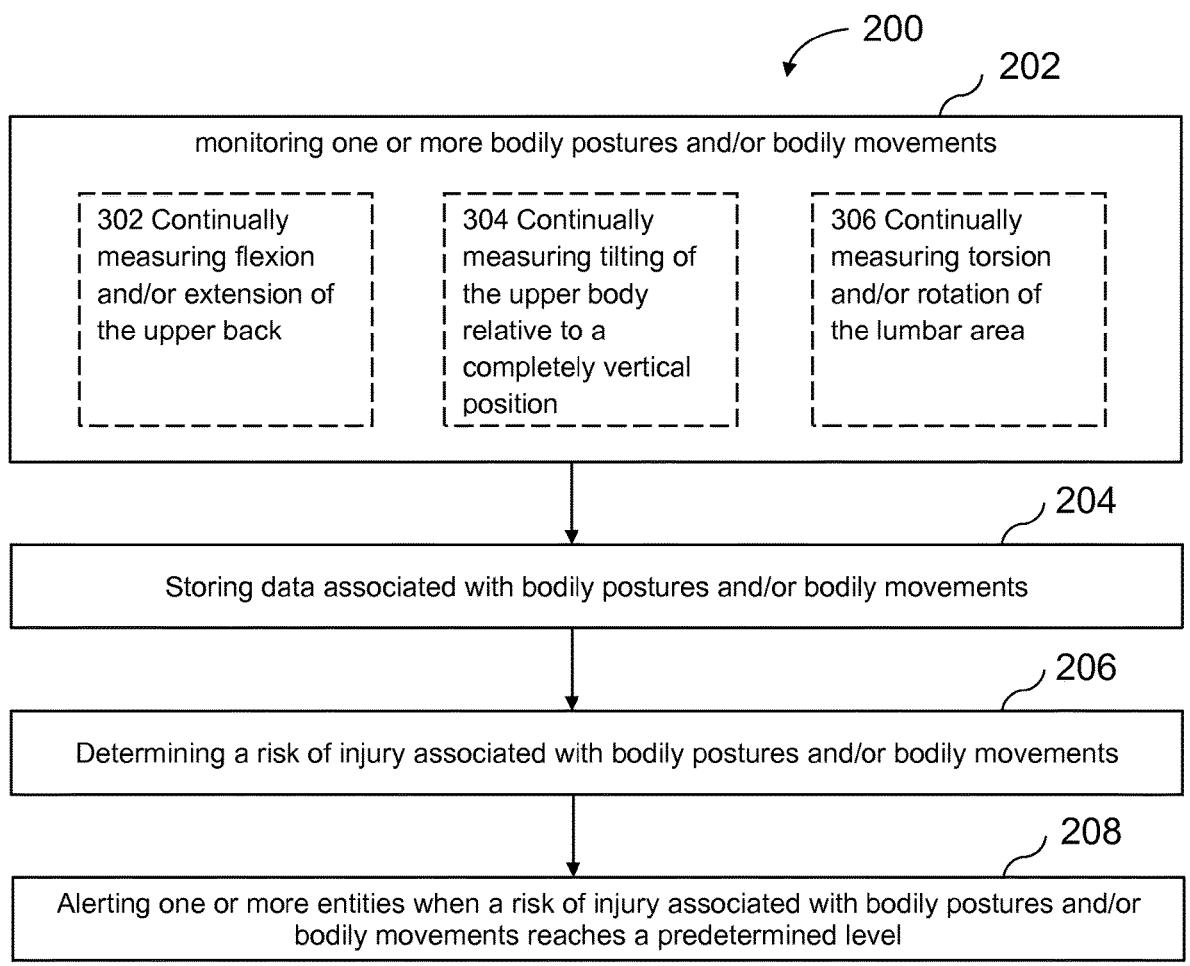
FIG. 3 depicts a block diagram of a method for the prevention of bodily injuries according to an embodiment of the invention.

FIG. 3 is a block diagram of various embodiments of a method for preventing bodily injuries. In one embodiment, method 200 may include one or more operations including continually measuring flexion and/or extension of the upper back 302, continually measuring tilt of the upper body relative to a completely vertical position 304, and continually measuring torsion and/or rotation of the lumbar area 306. The following embodiments and descriptions are for illustrative purposes only and are not intended to limit the scope of the apparatuses and methods for the prevention of bodily injuries.

In some embodiments, continually measuring flexion and/or extension of the upper back at block 302 may be performed using a strain gauge. For example, high elongation strain gauges may be positioned adjacent to the user's upper back by embedding the high elongation strain gauges into the torso support module 108. In some embodiments, the flexion and/or extension measured includes flexion and/or extension of the upper spine, shoulders, and/or any combination thereof. Flexion and/or extension may be measured in the sagittal plane, the coronal plane, the transverse plane, and/or any combination thereof. Generally, it is preferable that flexion and/or extension are measured in at least the sagittal plane for the upper back. However, flexion and/or extension may be measured for any joint of the body and may be measured in any plane or combination of planes. In some embodiments, the strain gauges are calibrated for use with the unique physiology of one or more users. Measurements associated with flexion and/or extension may be taken with any sensing device known in the art that is suitable for this purpose.

In some embodiments, continually measuring tilt of the upper body relative to a completely vertical position at block 304 may be performed using one or more inclinometers. For example, an inclinometer may be positioned adjacent to the user's middle or lower back by placing the inclinometer within the cavity of the main housing 102 of FIG. 1b. In some embodiments, an inclinometer for measuring tilt of the upper body will measure tilt using a full spherical coordinate system (e.g., the inclinometer will measure not only fore and aft leaning but also side to side leaning). In some embodiments, one or more inclinometers are calibrated for use with the unique physiology of one or more users. Measurements associated with tilting may be taken with any sensing device known in the art that is suitable for this purpose.

In some embodiments, continually measuring torsion and/or rotation of the lumbar area at block 306 may be performed using one or more yaw sensor or accelerometer. For example, a yaw sensor may be positioned adjacent to the user's lower back by placing the yaw sensor within the cavity of the main housing 102 of FIG. 1b. In some embodiments, a yaw sensor will continually measure the angular velocity of the user's lumbar area. In other embodiments, continually measuring torsion of the lumbar area at block 306 may be performed using one or more accelerometers. For example, one or more accelerometers may be positioned adjacent to the user's shoulders by embedding the accelerometers within the torso support module 108 or placing the accelerometers within the cavity of the secondary upper housing 104 for the purpose of continually measuring torsion or rotation of the upper back. Conversely, one or more accelerometers may be positioned adjacent to the user's lumbar region by embedding the accelerometers within the lumbar support module 110 or within the cavity of the secondary lower housing 106 for the purpose of continually measuring torsion or rotation of the lumbar region. Measurements associated with torsion may be based off sensing a rate of change or may be based off sensing static bodily positions. For example, an embodiment that bases measurements off of sensing static body positions will sense that a body is under torsion in the lumbar area even if that body is completely motionless. Measurements associated with torsion may be taken with any sensing device known in the art that is suitable for this purpose.

FIG. 4 is a block diagram of various embodiments of a method for preventing bodily injuries. In one embodiment, method 400 may include one or more operations including monitoring one or more bodily postures and/or bodily movements 402, storing data associated with bodily postures and/or bodily movements 404, determining a risk of injury associated with bodily postures and/or bodily movements 406, alerting one or more entities when a risk of injury associated with bodily postures and/or bodily movements reaches a predetermined level 408, and transmitting data associated with bodily postures and/or bodily movements 410. In some embodiments, method 400 may include one or more alternative embodiments discussed with reference to method 200. The following embodiments and descriptions are for illustrative purposes only and are not intended to limit the scope of the apparatus and methods for the prevention of bodily injuries.

In some embodiments, the operation of transmitting data associated with bodily postures and/or bodily movements at block 410 may be performed automatically by one or more different types of a data transmitter. For example, the operation of transmitting data associated with bodily postures and/or bodily movements at block 410 may be performed by a transmitter configured to transmit data through one or more cellular networks, radio signals, Bluetooth® signals, satellites, WLAN networks, optical data transfer networks, or any other means of transmitting data. Preferably, the operation at block 410 is performed automatically in order to reduce the effort required to access the data and also to encourage the entities which will be receiving the data to analyze the data and continuously reduce the risk of injury associated with any particular job description by eliminating the need for or occurrence of risky bodily postures and/or bodily movements. In some embodiments, data may be transferred manually by removing a data storage device (e.g., an SD card) from the apparatus embodying the method and connecting it to a device capable of reading the data (e.g., a computer). In some embodiments, the operation of transmitting data associated with bodily postures and/or bodily movements at block 410 may include transmitting data associated with predetermined bodily postures, predetermined bodily movements, the speed and/or repetitiveness at which predetermined bodily postures are entered, the speed and/or repetitiveness at which predetermined bodily movements are executed, or any combination thereof. Other types of data transmitting devices known in the art may be used.

FIG. 5 is a block diagram of various embodiments of a method for preventing bodily injuries. In one embodiment, method 500 may include any of the operations of monitoring one or more bodily postures and/or bodily movements 502, storing data associated with bodily postures and/or bodily movements 504, determining a risk of injury associated with bodily postures and/or bodily movements 506, alerting one or more entities when a risk of injury associated with bodily postures and/or bodily movements reaches a predetermined level 508, tracking user location 510, and tracking panic button status 512. In some embodiments, method 500 may include one or more alternative embodiments discussed with reference to method 200. The following embodiments and descriptions are for illustrative purposes only and are not intended to limit the scope of the apparatuses and methods for the prevention of bodily injuries.

In some embodiments, the operation of tracking user location at block 510 may be performed by a Global Positioning System (GPS) receiver. For example, a GPS receiver may be embedded into the apparatus (e.g., within the cavity of main housing 102 of FIG. 1*b*), and may determine the approximate location of the user sequentially after predetermined amounts of time (e.g., every 60 seconds when the device is turned on). In some embodiments, the operation of tracking user location at block 510 may be performed by the trilateration and/or triangulation of available signals (e.g., signals transmitted from cellular network towers). It is generally preferred that the operation of tracking user location at block 510 is included in the method 500 because the user location data is potentially valuable for many reasons (e.g., exposing specific locations where a risk of injury associated with bodily postures and/or bodily movements is heightened, optimization of delivery routes, monitoring of employee location for use in simplification of work processes, and/or any combination thereof). The operation of tracking user location at block 510 may be performed by any other means known in the art.

In some embodiments, the operation of tracking panic button status at block 512 may be performed actively by determining the panic button status at predetermined time intervals, passively by standing by for a signal produced and transmitted by the apparatus only in the event that the panic button is activated, or any combination thereof. For example, tracking status of the panic button might be performed only passively and not actively in order to increase battery life. In a preferred embodiment, both the operations of tracking user location at block 510 and tracking panic button status at block 512 are included because in the event that a panic button is activated and a person is likely injured, information regarding that person's location will be useful for one or more entities to provide aid. For example, in industries that are highly dependent on physical labor and also cover vast areas (e.g., the logging industry, the farming industry) the combination of these two functions is particularly valuable. The operation of tracking panic button status at block 512 may be performed by any other means known in the art.

FIG. 6 is a block diagram of various embodiments of a method for preventing bodily injuries. In one embodiment, method 600 may include one or more operations including monitoring one or more bodily postures and/or bodily movements 602, storing data associated with bodily postures and/or bodily movements 604, determining a risk of injury associated with bodily postures and/or bodily movements 606, alerting one or more entities when a risk of injury associated with bodily postures and/or bodily movements reaches a predetermined level 608, and supporting and/or inhibiting improper bending of a body 610. In some embodiments, method 600 may include one or more alternative embodiments discussed with reference to method 200. The following embodiments and descriptions are for illustrative purposes only and are not intended to limit the scope of the apparatuses and methods for the prevention of bodily injuries.

In some embodiments, the operation of supporting and/or inhibiting improper bending of a body at block 610 may be performed by restricting the body from entering predetermined postures. For example, the operation of supporting and/or inhibiting improper bending of a body at block 610 may include restricting the user's body from leaning forward, which can contribute to stress of the lumbar region. In some embodiments, the operation of supporting and/or inhibiting improper bending of a body at block 610 may be performed by rigid members embedded within the lumbar support module 110. For example, some embodiments include an aluminum skeletal frame for supporting and inhibiting improper bending of the body. In other embodiments, the operation of supporting and/or inhibiting improper bending of a body at block 610 may be performed by an brace comprising elastic materials that limit forward leaning and/or motion of the spine. For example, such a brace comprising elastic might assist in setting spinal fusions while supporting the spine during occasions of heightened stress (e.g., while lifting a heavy load). Other means for supporting and/or inhibiting improper bending of a body known in the art may be used.

FIG. 7 is a system diagram of one or more software applications embodied in computer readable media for preventing bodily injuries. In some embodiments, system 700 may include one or more software applications 704 embodied in computer readable media 702 for performing operations 706 of monitoring bodily postures and/or bodily movements, storing data associated with bodily postures and/or bodily movements, determining a risk of injury associated with bodily postures and/or bodily movements, and alerting one or more entities when a risk of injury associated with bodily postures and/or bodily movements reaches a predetermined level. In some embodiments, system 700 may include one or more software applications 704 embodied in computer readable media 702 for performing operations 706 of any embodiment disclosed herein. In some embodiments, computer readable media 702 may include volatile memory, non-volatile memory, an electronic signal, a wireless signal, an optical signal, and/or other media.

Figure 8:
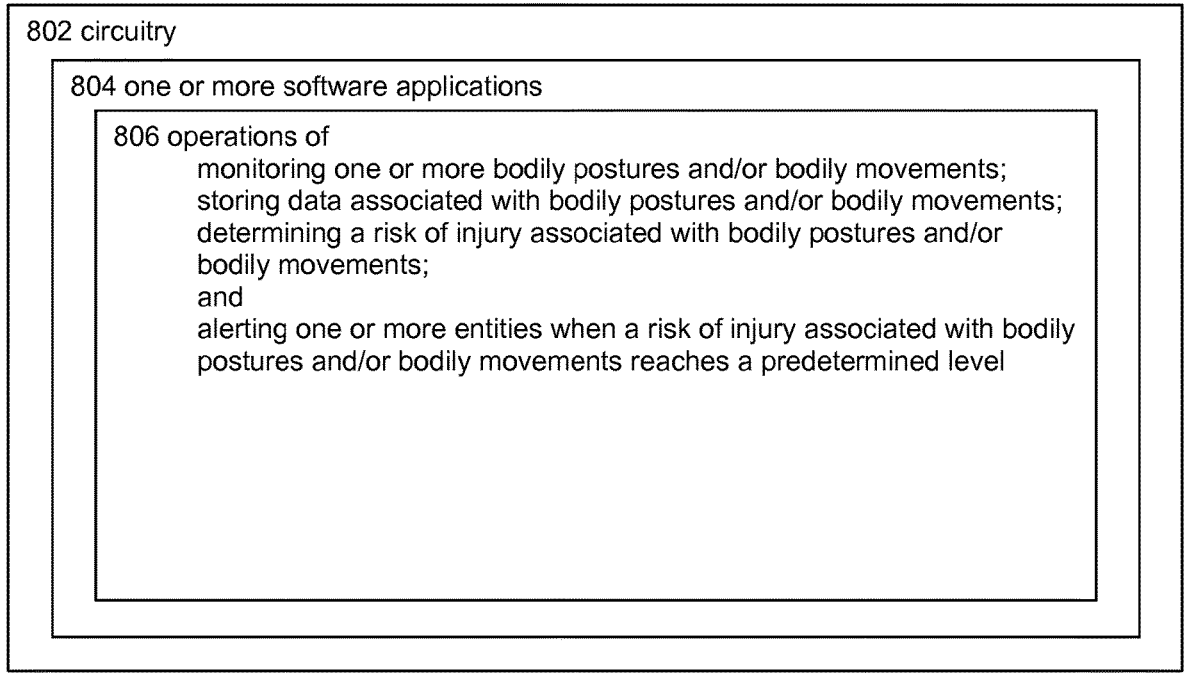
FIG. 8 is a system diagram of circuitry for preventing bodily injuries.

FIG. 8 is a system diagram of circuitry for preventing bodily injuries. In some embodiments, system 800 may include one or more software applications 804 embodied in circuitry 802 configured for performing operations 806 of monitoring bodily postures and/or bodily movements, storing data associated with bodily postures and/or bodily movements, determining a risk of injury associated with bodily postures and/or bodily movements, and alerting one or more entities when a risk of injury associated with bodily postures and/or bodily movements reaches a predetermined level. In some embodiments, system 800 may include one or more software applications 804 embodied in circuitry 802 configured for performing operations 806 of any embodiment disclosed herein. In some embodiments, circuitry 802 may include a printed circuit board. In some embodiments, circuitry 802 may include a general purpose computer which has been programed to perform a specific task. In some embodiments, circuitry 802 may include any other detailed plan or arrangement of electrical components designed to perform a specific task.

The words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Embodiments were chosen and described in order to best describe the principles of the invention and its practical application, thereby enabling others skilled in the relevant art to understand the claimed subject matter, the various embodiments and with various modifications that are suited to the particular use contemplated.

The teachings of the invention provided herein can be applied to other systems, not necessarily the system described above. The elements and acts of the various embodiments described above can be combined to provide further embodiments.

While the above description describes certain embodiments of the invention, and describes the best mode contemplated, no matter how detailed the above appears in text, the invention can be practiced in many ways. Details of the system may vary considerably in its implementation details, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

The invention claimed is:

1. An apparatus able to monitor postural information associated with a human body, the apparatus comprising:
   a back brace configured to support a portion of a human body while worn;
   a sensor configured to generate postural data indicative of tilt, torsion, flexion, or rotation of the portion of the human body;
   a processor configured to:
      identify a current posture of the portion of the human body by examining the postural data,
      determine an injury risk based on the postural data, the current posture, or any combination thereof, and
      compare the injury risk with a threshold level associated with a certain posture or a certain series of postures having a heightened risk of injury;
   a communication module configured to facilitate communication with a remote computing device; and
   a mechanical button configured to, upon selection, cause a location coordinate to be transmitted to the remote computing device by the communication module.

2. The apparatus of claim 1, wherein the processor is further configured to:
   determine the injury risk exceeds the threshold level, and
   cause a notification to be generated that alerts a user of the back brace that the injury risk exceeds the threshold level.

3. The apparatus of claim 2, wherein the processor is further configured to:
   cause an electronic notification to be transmitted to a computing device associated with another individual, wherein the electronic notification alerts the other individual that the injury risk of the user exceeds the threshold level.

4. The apparatus of claim 3, wherein the electronic notification is an email message.

5. The apparatus of claim 2, wherein the notification is a visual notification, an audible notification, or a tactile notification.

6. The apparatus of claim 1, wherein the threshold level represents a tilt value, a torsion value, a flexion value, a rotation value, or any combination thereof.

7. The apparatus of claim 1, wherein the sensor is embedded within the back brace.

8. The apparatus of claim 1, wherein the sensor includes an inclinometer, a yaw sensor, an accelerometer, a strain gauge, a gyroscope, or any combination thereof.

9. An apparatus comprising:
   a back brace configured to support a lumbar region of a human body while worn;
   at least one sensor configured to generate postural data indicative of tilt, torsion, flexion, or rotation of the lumbar region of the human body;
   a processor configured to identify a current posture by examining the postural data;
   a communication module configured to facilitate communication with a remote computing device; and
   a mechanical button configured to, upon selection, cause a location coordinate to be transmitted to the remote computing device by the communication module, wherein the location coordinate is indicative of a location of the back brace.

10. The apparatus of claim 9, further comprising:
    a power source configured to supply power to the at least one sensor, the processor, the communication module, or any combination thereof.

11. The apparatus of claim 10, wherein the power source is replaceable or rechargeable via a power connector cable.

12. The apparatus of claim 9, wherein the communication module is further configured to:
    transmit at least some of the postural data to the remote computing device for further examination.

13. The apparatus of claim 12, wherein the remote computing device is a data server.

14. The apparatus of claim 9, wherein the processor is further configured to:
    determine an injury risk based on the current posture,
    compare the injury risk with a threshold level associated with a certain posture or a certain series of postures having a heightened risk of injury,
    determine the injury risk exceeds the threshold level, and
    cause a notification to be generated that alerts a user of the back brace that the injury risk exceeds the threshold level.

15. An apparatus comprising:
    a back brace configured to support a lumbar region of a human body;
    a first sensor configured to be disposed proximate to a thoracic region of the human body when the back brace is worn on the human body;
    a second sensor configured to be disposed proximate to the lumbar region of the human body when the back brace is worn on the human body;
    a processor configured to identify a current posture by examining postural data generated by the first and second sensors;
    a communication module configured to transmit at least some of the postural data to a computing device for further examination;

a Global Positioning System (GPS) receiver configured to generate location data comprised of discrete values indicative of a location of the back brace at corresponding points in time; and a mechanical button configured to, upon selection, cause a location coordinate indicative of a current location to be transmitted to the computing device by the communication module.

16. The apparatus of claim 15, wherein the processor is further configured to:
   determine an injury risk based on the current posture,
   compare the injury risk to a threshold level associated with a certain posture having a heightened risk of injury, and
   cause a notification to be generated responsive to a determination that the injury risk exceeds the threshold level.

17. The apparatus of claim 15, wherein the communication module is a wireless local area network (WLAN) transmitter circuit or a Bluetooth transmitter circuit that enables transmission of the at least some postural data to the computing device.

18. The apparatus of claim 15, wherein the processor is further configured to:
   identify, based on the postural data and the location data, a specific location where the injury risk is heightened.

* * * * *